(12) United States Patent
De Lacharriere et al.

(10) Patent No.: US 7,351,699 B1
(45) Date of Patent: Apr. 1, 2008

(54) USE OF DHEA OR PRECURSORS OR METABOLIC DERIVATIVES THEREOF AS A DEPIGMENTING AGENT

(75) Inventors: Olivier De Lacharriere, Paris (FR); Stephanie Nouveau, Boulogne (FR)

(73) Assignee: L'Oreal, Paris (FR)

( * ) Notice: Subject to any disclaimer, the term of this patent is extended or adjusted under 35 U.S.C. 154(b) by 708 days.

(21) Appl. No.: 09/686,997

(22) Filed: Oct. 12, 2000

(30) Foreign Application Priority Data

Oct. 13, 1999 (FR) .................................. 99 12773

(51) Int. Cl.
 *A61K 31/56* (2006.01)
 *A61K 8/02* (2006.01)
 *A61K 8/18* (2006.01)

(52) U.S. Cl. ...................... 514/171; 514/169; 514/177; 514/182; 424/401; 424/59

(58) Field of Classification Search ................ 424/401, 424/59, 169, 171; 514/169, 171, 177, 182
 See application file for complete search history.

(56) References Cited

U.S. PATENT DOCUMENTS

| 4,316,033 | A |   | 2/1982  | Ching |         |
|-----------|---|---|---------|-------|---------|
| 4,328,346 | A |   | 5/1982  | Chung et al. |  |
| 4,496,556 | A |   | 1/1985  | Orentreich |    |
| 4,542,129 | A |   | 9/1985  | Orentreich |    |
| 4,617,390 | A |   | 10/1986 | Hoppe et al. |  |
| 5,607,692 | A | * | 3/1997  | Ribier et al. ................. | 424/401 |
| 5,670,487 | A | * | 9/1997  | Grollier et al. ............... | 424/59 |
| 5,776,438 | A | * | 7/1998  | Tokue et al. .................. | 424/59 |
| 5,824,671 | A |   | 10/1998 | Labrie |         |
| 5,869,090 | A | * | 2/1999  | Rosenbuam ................ | 424/449 |
| 5,900,242 | A | * | 5/1999  | Breton et al. ............... | 424/401 |
| 5,942,531 | A | * | 8/1999  | Diaz et al. .................. | 514/394 |
| 5,989,568 | A | * | 11/1999 | Breton et al. ............... | 424/401 |
| 6,149,933 | A | * | 11/2000 | Nelson ........................ | 424/441 |
| 6,486,147 | B2 | * | 11/2002 | Baldo et al. ................. | 514/178 |

FOREIGN PATENT DOCUMENTS

| DE | EP 0087098 A2 | 8/1983 |
| EP |     0389377 A1 | 9/1990 |
| EP |     0517104 A1 | 12/1992 |
| EP |     0570838 A1 | 11/1993 |
| EP |     0655453 A1 | 5/1995 |
| EP |    0 723 775  | 7/1996 |
| EP |     0796851 A1 | 9/1997 |
| FR |     2528420 A1 | 6/1982 |
| FR |     2581542 A1 | 11/1986 |
| FR | EP 0354145 A1 | 2/1990 |
| FR |     2639347 A1 | 5/1990 |
| FR | EP 0392883 A1 | 10/1990 |
| FR |     2657351 A1 | 7/1991 |
| FR | EP 0524109 A1 | 1/1993 |
| FR | EP 0723775 A1 | 7/1996 |
| FR | EP 0738510 A2 | 10/1996 |
| FR | EP 0756866 A1 | 2/1997 |
| FR | EP 0660701 A1 | 5/1997 |
| FR |    2 760 362  | 9/1998 |
| FR | EP 0875495 A1 | 11/1998 |
| FR | EP 0895779 A1 | 2/1999 |
| FR |    2 777 181  | 10/1999 |
| FR |    2 777 181 A | 10/1999 |
| JP |      60142908 A | 7/1985 |
| JP |      60 161912  | 8/1985 |
| JP |      60161912   | 8/1985 |
| JP |      07 196467  | 8/1995 |
| JP |       7196467 A | 8/1995 |
| WO | WO 94/06404   | 3/1994 |
| WO | WO 97 10255   | 3/1997 |
| WO | WO 97/12597   | 4/1997 |
| WO | WO 97/13500 A2 | 4/1997 |
| WO | WO 98/35973 A1 | 8/1998 |
| WO | WO 99/10318 A1 | 3/1999 |
| WO | WO 99/22707 A1 | 5/1999 |
| WO | WO 99/32077 A1 | 7/1999 |

OTHER PUBLICATIONS

Hadley et al., "Hormonal control of melanogenesis," Pigm. and Pigm. Disord., ed. Norman Levine, 1993, pp. 95-114.*

E. E. Baulieu et al, *Dehydroepiandrosterone (DHEA), DHEA sulfate, and aging: Contribution of the DHEAge Study to a Sociobiomedical Issue*, PNAS, Apr. 11, 2000, vol. 97, No. 8, pp. 4279-4284, XP002141516.

Shinchi Kawai, et al, *Dehydroepiandrosterone Inhibits B16 Mouse Melanoma Cell Growth By Induction or Differentiation*, Chemical Abstracts, vol. 123, No. 7, Aug. 14, 1995, XP-002141517.

Patent Abstracts of Japan, vol. 1995, No. 11, Dec. 26, 1995, JP07195467.

Patent Abstracts of Japan, vol. 009, No. 331, Dec. 25, 1985, JP60161912.

Chemical Abstracts, vol. 123, No. 7, Aug. 14, 1995, Columbus, OH, Abstract No. 75142q. Shinichi Kawai, et al.: "Dehydroepiandrosterone Inhibits B16 Mouse Melanoma Cell Growth By Induction or Differentiation" XP002141517.

(Continued)

*Primary Examiner*—Shengjun Wang
(74) *Attorney, Agent, or Firm*—Oblon, Spivak, McClelland, Maier & Neustadt, P.C.

(57) ABSTRACT

The use of DHEA or at least one of its biological precursors or of its metabolic derivatives in or for the manufacture of a composition for topical application to the skin, as a pigmentation regulator for the skin or its superficial growths, especially as a depigmenting and/or bleaching agent for the skin, in particular in the treatment of pigmentation marks, and as a pro-pigmenting agent for superficial body growths.

25 Claims, 1 Drawing Sheet

OTHER PUBLICATIONS

Anticancer Research, vol. 15, No. 2, 1995, "Dehydroepiandrosterone Inhibits B16 Mouse Melanoma Cell Growth By Induction or Differentiation" pp. 427-432.

E.E., Baulieu, et al.: "Dehydroepiandrosterone (DHEA), DHEA Sulfate and Aging: Contribution of the DHEAge Study to a Sociobiomedical Issue" Proceedings of the National Academy of Sciences of USA, vol. 97, No. 8, Apr. 11, 2000, pp. 4279-4284, XP002141516.

National Academy of Science, U.S., ISSN: 0027-8424, "Life In A Ligand Sphere", pp. 4283-4287, May 1994.

* cited by examiner

USE OF DHEA OR PRECURSORS OR METABOLIC DERIVATIVES THEREOF AS A DEPIGMENTING AGENT

BACKGROUND OF THE INVENTION

1. Field of the Invention

The present invention relates to the use of DHEA or at least one of biological precursor thereof or metabolic derivative thereof in or for the manufacture of a composition for topical application to the skin, as a pigmentation regulator for the skin or its superficial growths, especially a depigmenting and/or bleaching agent for the skin, in particular, for the treatment of pigmentation marks.

2. Description of the Background

The color of human skin depends on a variety of factors and, in particular, the seasons of the year, race and sex, and it is mainly determined by the nature and concentration of melanin produced by the melanocytes. Melanocytes are specialized cells which synthesize organized melanin by means of specific organelles, the melanosomes. In addition, at different periods in their life, certain individuals develop darker and/or more colored blemishes on the skin and more especially on the hands and the neck and shoulders, making the skin non-uniform. These blemishes are also due to a large concentration of melanin in the keratinocytes located at the skin surface.

The mechanism for the formation of skin pigmentation, that is to say the formation of melanin, is particularly complex and schematically involves the following main steps:

Tyrosine→Dopa→Dopaquinone→Dopachrome→Melanin

Tyrosinase (monophenol dihydroxyl phenylalanine: oxygen oxidoreductase EC 1.14.18.1) is the essential enzyme involved in this reaction sequence. It catalyzes the reaction for the conversion of tyrosine into dopa (dihydroxyphenylalanine) by virtue of its hydroxylase activity and the reaction for the conversion of dopa into dopaquinone by virtue of its oxidase activity. This tyrosinase acts only when it is in the mature state, under the action of certain biological factors.

A substance is recognized as being depigmenting if it acts directly on the vitality of the epidermal melanocytes in which melanogenesis takes place and/or if it interferes with one of the steps in the biosynthesis of melanin either by inhibiting one of the enzymes involved in melanogenesis or by becoming intercalated as a structural analog of one of the chemical compounds in the melanin synthesis chain, whereby this chain may then be blocked and thus ensure depigmentation.

The substances most commonly used as depigmenting agents are, more particularly, hydroquinone and its derivatives, in particular its ethers such as hydroquinone monomethyl ether and monoethyl ether. Although they have a certain level of efficacy, these compounds are, unfortunately, not free of side effects on account of their toxicity, which can make them difficult or even hazardous to use. This toxicity arises from the fact that they interfere with fundamental mechanisms of melanogenesis by killing cells which then risk disrupting their biological environment and which consequently force the skin to eliminate them by producing toxins. Thus, hydroquinone is a compound which is particularly irritating and cytotoxic to melanocytes, and whose total or partial replacement has been envisaged by many workers in the field.

It is most particularly sought to use harmless topical depigmenting substances which have good efficacy, with a view to treating regional hyperpigmentations caused by melanocyte hyperactivity, such as idiopathic melasmas, occurring during pregnancy ("pregnancy mask" or chloasma) or during oestroprogestative contraception, localized hyperpigmentations caused by hyperactivity and proliferation of benign melanocytes, such as senile pigmentation marks known as actinic lentigo, accidental hyperpigmentations or depigmentations, possibly due to photosensitization or to post-lesional cicatrization, as well as certain leukodermias, such as vitiligo. For the latter, in which the cicatrizations can result in a scar which gives the skin a whiter appearance and leukodermias, failing being able to repigment the damaged skin, the regions of residual normal skin are depigmented in order to give the skin as a whole a uniform white complexion.

The depigmenting substances also find an application in the bleaching of superficial body growths, in particular of hairs which it may be desirable to lighten in order to make them less visible.

Thus, there is still a need for a novel bleaching agent for human skin or its superficial growths, which acts as effectively as the known agents, but which does not have their drawbacks, i.e. which is non-irritant, non-toxic and/or non-allergenic to the skin and/or its superficial growths.

Conversely, it is known that, in most populations, maintaining a constant hair color is an important aspiration which may either result from aesthetic considerations, or may be justified by the need to overcome a pigmentation anomaly of pathological origin. This is thus the case for canities, or greying of the hair, which is thought to be associated with an autoimmune disease, in particular vitiligo.

Topically-acting pro-pigmenting agents have been proposed before, either in the field of artificial coloration by supplying exogenous dyes, such as DHA, which are supposed to give the skin or superficial body growths a coloration which is as close as possible to their natural coloration, or in the field of natural coloration, by stimulating melanogenesis with or without UV action.

DHEA, or dehydroepiandrosterone, is a natural steroid produced essentially by the corticoadrenal glands. It is known for its anti-ageing properties, associated with its capacity to promote epidermal keratinization (JP-07 196 467) and to combat osteoporosis (U.S. Pat. No. 5,824,671), or alternatively in the treatment of dry skin, on account of its ability to increase the endogenous production and secretion of sebum and to reinforce the skin's barrier effect (U.S. Pat. No. 4,496,556). DHEA is also described in the treatment of obesity and diabetes (WO 97/13500). It has also been proposed to use DHEA sulfate to combat alopecia (JP-60 142 908) and to treat various signs of ageing such as wrinkles, loss of skin radiance and slackening of the skin (EP-0 723 775). However, it has never yet been suggested that DHEA or at least one of its precursors or derivatives might have regulatory activity on pigmentation by acting directly on melanogenesis.

SUMMARY OF THE INVENTION

Now, the Inventors have found, unexpectedly, that DHEA and its biological precursors or metabolic derivatives have regulatory activity on the pigmentation of the skin and its superficial growths.

In particular, it has been demonstrated that DHEA has depigmenting activity, even at low concentrations, without showing any cytotoxicity. In addition, DHEA can be used in particular in the treatment of canities.

A subject of the present invention is thus the cosmetic use of DHEA or at least one of its biological precursors or metabolic derivatives in a composition for topical application to the skin or its superficial growths, to regulate the pigmentation of the skin or superficial body growths.

In particular, when this composition is applied to the skin, DHEA or at least one of its biological precursors or metabolic derivatives can be used as depigmenting and/or bleaching agents for the skin and/or to improve the homogeneity of the color of the skin. As a variant, when the composition is applied to superficial body growths, it may be useful as a propigmenting agent for the superficial body growths, in particular the hair.

Accordingly, the present invention provides a method of regulating the pigmentation of skin and/or superficial body growths, comprising applying DHEA or at least one biological precursor thereof or metabolic derivative thereof to the skin and/or superficial body growths.

The present invention additionally provides a method of depigmenting and/or bleaching for the skin and/or to improving the homogeneity of the color of the skin, comprising applying DHEA or at least one biological precursor thereof or metabolic derivative thereof to the skin.

The present invention also provides a method of propigmenting superficial body growths, comprising applying DHEA or at least one biological precursor thereof or metabolic derivative thereof to superficial body growths.

A subject of the invention is also the use of DHEA or at least one of its biological precursors or metabolic derivatives for the manufacture of a composition for topical application to the skin or its superficial growths, which is intended to regulate the pigmentation of the skin or superficial body growths.

In particular, when this composition is applied to the skin, it may be used for depigmenting the skin, especially for treating of pigmentation marks, in particular actinic lentigo. As a variant, when it is applied to superficial body growths, the composition may be used for the treatment of canities.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
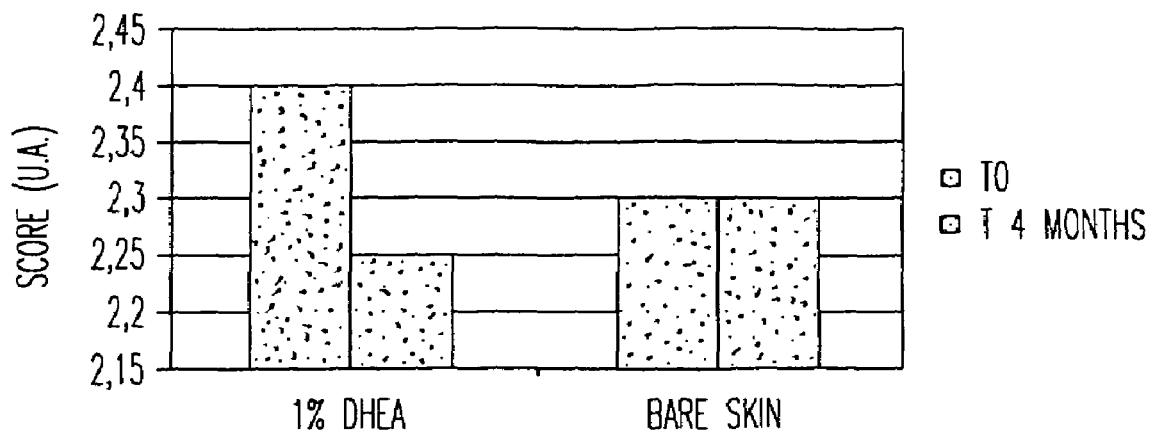
FIG. 1: clinical score of pigmentation marks as described in Example 2.

The DHEA which can be used according to the invention is available, for example, from Sigma or from Akzo Nobel.

Examples of biological precursors of DHEA include DHEA cholesterol, pregnenolone, 17α-hydroxypregnenolone, 5-androstenediol, DHEA sulfate, 17α-hydroxypregnenolone sulfate and 5-androstenediol sulfate, without this list being limiting.

The term "metabolic derivatives of DHEA" refers to, for example, 5-androstene-3β,17β-diol (or adiol), 5-androstene-3β,17β-diol sulfate and 4-androstene-3,17-dione, without this list being limiting.

The composition containing the DHEA or at least one of its biological precursors or metabolic derivatives is suitable for topical use and it thus contains a physiologically acceptable medium, i.e. a medium which is compatible with the skin and its superficial growths such as hairs or the hair.

This composition contains an amount of DHEA, or its biological precursor or metabolic derivative, which is sufficient to obtain the desired effect. It can thus contain from $10^{-6}$% to 10% by weight, preferably from 0.1% to 5% by weight and better still about 1% by weight, of DHEA or its biological precursor or metabolic derivative, relative to the total weight of the composition. These ranges include all specific values and subranges therebetween, such as $10^{-5}$, 0.01, 0.05, 0.2, 0.5 and 2%, relative to the total weight of the composition.

The composition of the invention may be in any pharmaceutical form typically used for topical application, in particular in the form of an aqueous or aqueous-alcoholic solution, an oil-in-water or water-in-oil or multiple emulsion, an aqueous gel or a liquid, pasty or solid anhydrous product.

This composition may be relatively fluid and have the appearance of a white or colored cream, an ointment, a milk, a lotion, a serum, a paste or a foam. It may optionally be applied to the skin in aerosol form. It may also be in solid form and, for example, in the form of a stick. It can be used as a care product and/or as a make-up product. As a variant, the composition can be used in the form of a shampoo or a conditioner.

In a known manner, the composition of the invention can also contain the adjuvants which are usual in the cosmetics and dermatological fields, such as hydrophilic or lipophilic gelling agents, hydrophilic or lipophilic active agents, preserving agents, antioxidants, solvents, fragrances, fillers, screening agents, pigments, odor absorbers and dyestuffs. The amounts of these various adjuvants are those conventionally used in the fields considered, and, for example, from 0.01 to 20% of the total weight of the composition. Depending on their nature, these adjuvants can be introduced into the fatty phase, into the aqueous phase, into lipid vesicles and/or into nanoparticles.

As will be readily appreciated, a person skilled in the art will take care to select these optional additional active or inactive compounds, and/or the amount thereof, such that the advantageous properties of DHEA or its precursors or derivatives are not, or are not substantially, adversely affected by such additional materials.

When the composition according to the invention is an emulsion, the proportion of the fatty phase can range from 0.5 to 80% by weight, and preferably from 5 to 50% by weight, relative to the total weight of the composition. These ranges for the amount of fatty phase include all specific values and subranges therebetween, such as 1, 2, 10, 25 and 75% by weight, relative to the total weight of the composition. The oils, the emulsifiers and the co-emulsifiers used in the composition in emulsion form are chosen from those conventionally used in the field considered. The emulsifier and the co-emulsifier are present in the composition in a proportion ranging from 0.3 to 30% by weight, and preferably from 0.5 to 20% by weight, relative to the total weight of the composition.

As oils which can be used in the invention, mention may be made of mineral oils (liquid petroleum jelly), oils of plant origin (avocado oil, soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax, ozokerite) can also be used as fatty substances.

As emulsifiers and co-emulsifiers which can be used in the invention, mention may be made, for example, of fatty acid esters of polyethylene glycol, such as PEG-20 stearate, and fatty acid esters of glycerol, such as glyceryl stearate.

As hydrophilic gelling agents, mention may be made in particular of carboxyvinyl polymers (carbomer), acrylic copolymers such as acrylate/alkylacrylate copolymers, polyacrylamides, polysaccharides, natural gums and clays, and, as lipophilic gelling agents, mention may be made of modified clays such as bentones, metal salts of fatty acids, hydrophobic silica and polyethylenes.

Polyols vitamins, keratolytic agents and/or desquamating agents, anti-inflammatory agents, calmants and mixtures thereof can be used in particular as active agents. Also, although DHEA and its precursors or metabolic derivatives alone have depigmenting activity which justifies their use as sole depigmenting active agent in a whitening composition, other depigmenting agents can also be added to the composition according to the invention, which allows the latter to be used at lower doses. In the event of incompatibility, at least some of these active agents can be incorporated into spherules, in particular ionic or non-ionic vesicles and/or nanoparticles (nanocapsules and/or nanospheres), so as to isolate the incompatible active agents among them from each other in the composition.

According to one preferred embodiment of the invention, the compositions containing DHEA or its precursors or derivatives also contain at least one UV screening agent and/or one other depigmenting agent and/or one keratolytic agent.

UV screening agents which may be used in the present invention include:

(1) dibenzoylmethane derivatives, and in particular 4-(tert-butyl)-4'-methoxydibenzoylmethane, in particular the product sold under the trade name "Parsol 1789" by the company Givaudan, and 4-isopropyldibenzoylmethane, this screening agent being sold under the name "Eusolex 8020" by Merck;

(2) benzylidenecamphor-based UVA-active screening agents, a particularly preferred example of which is benzene-1,4-bis(3-methylidenecamphor-10-sulphonic acid) such as the product sold under the name Mexoryl SX by Chimex, described in particular in patent applications FR-A-2 528 420 and FR-A-2 639 347;

(3) benzylidenecamphor-based UVB-active screening agents, and in particular 4-methyl-benzylidenecamphor, which is available from Merck under the trade name Eusolex 6300;

(4) benzimidazole-type or benzoxazole-type UVA-active screening agents, such as 2-phenyl-benzimidazole-5-sulphonic acid, which is available from Merck under the trade name Eusolex 232;

(5) benzophenone derivatives which may he chosen advantageously from the group consisting of: 2-hydroxy-4-methoxybenzophenone, also known as oxyhenzone (benzophenone-3), such as the product sold under the name Uvinul M40 by BASF; and 2-hydroxy-4-methoxybenzophenone-5-sulphonic acid, also known as sulisobenzone (benzophenone-4), such as the product sold under the name Uvinul MS 40 by BASF, as well as its sodium sulphonate form (benzophenone-5);

(6) silane derivatives or polyorganosiloxanes containing a benzophenone group, such as those described in EP-A-0 389 377, FR-A-2 657 351 and EP-A-0 655 453;

(7) benzotriazoles and benzotriazole silicones, preferably those described in U.S. Pat. No. 4,316,033, U.S. Pat. No. 4,328,346, EP-B-0 354 145, EP-B-0 392 883 and EP-B-0 660 701 (incorporated herein by reference);

(8) the triazine derivatives described in U.S. Pat. No. 4,617,390 and patent applications EP-A-087 098, EP-A-0 517 104, EP-A-0 570 838 and EP-A-0 796 851 (all incorporated herein by reference), in particular 2,4,6-tris[p-(2'-ethylhexyl-1'-oxycarbonyl)anilino]-1,3,5-triazine sold in particular under the trade name Uvinul T 150 by BASF;

(9) cinnamic acid derivatives such as 2-ethylhexyl paramethoxycinnamate, sold in particular under the trade name Parsol MCX by Givaudan;

(10) alkyl 2-cyano-3,3-diphenylacrylates, and preferably octocrylene sold under the name Uvinul N 539 by BASF;

(11) the compound of formula I below, or 2-(2H-benzotriazol-2-yl)-4-methyl-6-[2-methyl-3[1,3,3,3-tetramethyl-1-[(trimethylsilyl)oxy]-disiloxanyl]propynyl]phenol, described in patent application EP-A-0 392 883 (incorporated herein by reference):

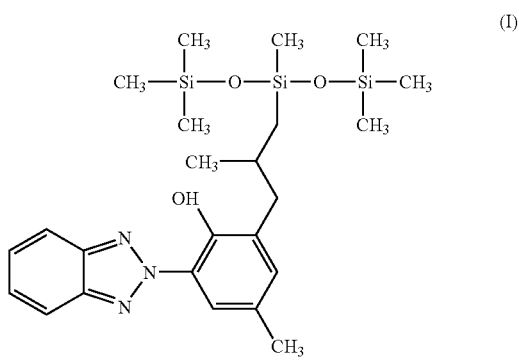

(12) and mixtures thereof.

The publications cited above relating to sunscreening agents are incorporated herein by reference.

As other depigmenting agent, the compositions according to the invention can comprise, for example, at least one of the following compounds: kojic acid; ellagic acid; arbutin and its derivatives such as those described in patent applications EP-895 779 and EP-524 109; hydroquinone; aminophenol derivatives such as those described in WO 99/10318 and WO 99/32077, and in particular N-cholesteryloxycarbonyl-para-aminophenol and N-ethyloxycarbonyl-para-aminophenol; iminophenol derivatives, in particular those described in WO 99/22707; L-2-oxothiazolidine-4-carboxylic acid or procysteine, as well as its salts and esters; ascorbic acid and its derivatives, in particular ascorbyl glucoside; and plant extracts, in particular extract of liquorice, of mulberry and of skullcap, without this list being limiting. The publications cited above are incorporated herein by reference.

A subject of the invention is thus also a composition comprising, in a physiologically acceptable medium, DHEA or at least one of its biological precursors or metabolic derivatives and at least one depigmenting agent chosen from: kojic acid; ellagic acid; arbutin and its derivatives; hydroquinone; aminophenol derivatives such as N-cholesteryloxycarbonyl-para-aminophenol and N-ethyloxycarbonyl-para-aminophenol; iminophenol derivatives; L-2-oxothiazolidone-4-carboxylic acid or procysteine, as well as its salts and esters; and plant extracts, in particular extract of liquorice, of mulberry and of skullcap.

The keratolytic agents which may be used in the compositions according to the invention in particular comprise α-hydroxy acids such as citric acid, lactic acid, glycolic acid, mandelic acid, malic acid and tartaric acid; O-hydroxy acids and in particular salicylic acid and its derivatives described in patent applications FR-A-2 581 542, EP-875 495, WO 98/35973 and EP-756 866; α-keto acids and β-keto acids; retinoids and in particular retinol and retinyl esters; HMG-CoA reductase inhibitors as described in patent application EP-738 510; and sugar derivatives such as those described in patent application EP-853 472, and in particular O-octanoyl-6'-β-D-maltose. The publications cited above are incorporated herein by reference.

These compositions in particular constitute protective, treatment or care creams for the face, for the hands or for the body, protective or care body milks, lotions, gels or mousses for skincare or skin treatment, cleansing or disinfecting lotions, bath compositions, foundations and tinted creams. In the latter cases, the composition contains pigments.

EXAMPLES

Having generally described this invention, a further understanding can be obtained by reference to certain specific examples which are provided herein for purposes of illustration only and are not intended to be limiting unless otherwise specified.

Example 1

Composition Based on DHEA

The composition below, in which the proportions of the various constituents are indicated as percentages by weight, was prepared:

| | |
|---|---|
| DHEA | 2% |
| Propylene glycol isostearate | 13% |
| Polyethylene glycol (8 EO) | 5% |
| Propylene glycol | 3% |
| Pentylene glycol | 3% |
| Glyceryl stearate and polyethylene glycol stearate (100 EO) | 5% |
| oxyethylenated sorbitan monostearate (20 EO) | 0.5% |
| Oxyethylenated (20 EO) oxypropylenated (5 PO) cetyl alcohol | 1% |
| Gelling agents | 0.5% |
| $C_{12-15}$ alkyl benzoates | 4% |
| Ethanol | 3% |
| Sodium hydroxide | 0.12% |
| Preserving agents | 0.7% |
| Water qs | 100% |

Example 2

Demonstration of the Depigmenting Activity of DHEA a—Protocol

A gelled oil-in-water emulsion, containing 1% by weight of DHEA as sole active agent, was tested on a group of 20 women from 55 to 70 years old. The emulsion was applied morning and evening for four months to the back of one hand.

The marks present on the skin were evaluated before and after treatment by visual observation made by an expert, giving the marks an overall score from 0 to 7 as a function of their number, their size and their intensity (clinical evaluation).

They were also evaluated by colorimetry, using a Minolta CR200 chronometer (biophysical evaluation). This apparatus describes the colors in a three-dimensional space, using the system of coordinates L, a* and b* recommended by the International Commission on Illumination, in which L* represents the luminance or clarity of the color (O corresponding to white and 100 to black), a* is the separation component between green (negative) and red (positive) and is correlated to the skin erythema, and b* varies from blue (negative) to yellow (positive) and represents the skin pigmentation. This parameter b* was used to evaluate the change in the marks in the course of the treatment. It is the result of the average of six individual measurements taken per zone and per measurement period.

b—Results

Clinical evaluation: the graph illustrated in FIG. 1 shows an improvement in the overall clinical score of the pigmentation marks on the hand treated with DHEA, whereas this score is constant on the untreated hand.

Figure 2:
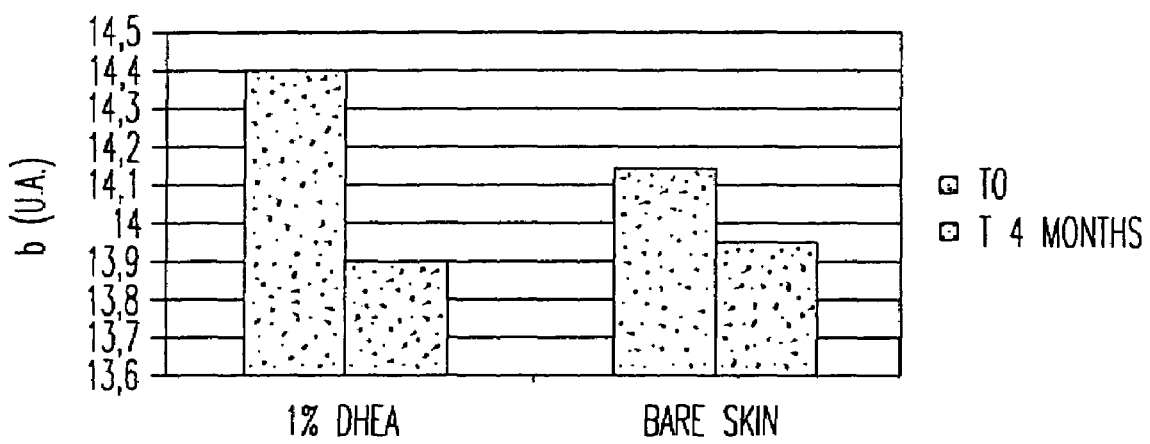
FIG. 2: decrease in component b of the color of the skin as described in Example 2.

Biophysical evaluation: the graph illustrated in FIG. 2 shows a decrease in the component b of the color of the skin, and thus a reduction in the pigmentation of the skin, which is greater on the hand treated with DHEA than on the untreated hand.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 9912773, filed on Oct. 13, 1999, and incorporated herein by reference in its entirety.

The invention claimed is:

1. A method of pro-pigmenting human hair in need of pro-pigmenting, comprising applying DHEA or at least one biological precursor thereof or metabolic derivative thereof to the human hair, wherein said metabolic derivative thereof is selected from the group consisting of 5-androstene-3β, 17β-diol, 5-androstene-3β,17β-diol sulfate and 4-androstene-3,17-dione and said biological precursor thereof is selected from the group consisting of pregnenolone, 17α-hydroxypregnenolone, DHEA sulfate, and 17α-hydroxypregnenolone sulfate.

2. The method of claim 1, wherein the DHEA or at least one of biological precursor thereof or metabolic derivative thereof is applied in the form of a composition.

3. The method of claim 1, wherein the DHEA or at least one biological precursor thereof or metabolic derivative thereof is applied in the form of a composition comprising from $10^{-6}$% to 10% by weight, relative to the total weight of the composition, of the DHEA or at least one of biological precursor thereof or metabolic derivative thereof.

4. The method of claim 3, wherein the composition comprises from 0.1% to 5% by weight, relative to the total weight of the composition, of the DHEA or at least one biological precursor thereof or metabolic derivative thereof.

5. The method of claim 3, wherein the composition comprises about 1% by weight, relative to the total weight of the composition, of the DHEA or at least one biological precursor thereof or metabolic derivative thereof.

6. The method of claim 2, wherein the composition further comprises at least one UV screening agent and/or one depigmenting agent and/or one keratolytic agent.

7. The method of claim 6, wherein the composition further comprises the UV screening agent selected from the group consisting of dibenzoylmethane derivatives, benzylidenecamphor-based UVA-active screening agents, benzylidenecamphor-based UVB-active screening agents, benzimidazole-type or benzoxazole-type UVA-active screening agents, benzophenone derivatives, silane derivatives, polyorganosiloxanes containing a benzophenone group, benzotriazoles, benzotriazole silicones, triazine derivatives, cinnamic acid derivatives, alkyl 2-cyano-3,3-diphenylacrylates, octocrylene, the compound of formula I below,

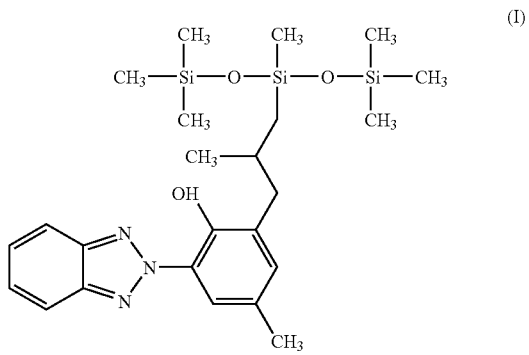

and mixtures thereof.

8. The method of claim 6, wherein the composition further comprises said depigmenting agent selected from the group consisting of kojic acid, ellagic acid, arbutin and derivatives thereof, hydroquinone, aminophenol derivatives, iminophenol derivatives, L-2-oxothiazolidone-4-carboxylic acid and salts or esters thereof, procysteine and salts or esters thereof, ascorbic acid and derivatives thereof, and plant extracts.

9. The method of claim 6, wherein the composition further comprises said keratolytic agent selected from the group consisting of α-hydroxy acids, β-hydroxy acids, α-keto acids, β-keto acids, retinoids, HMG-COA reductase inhibitor, and sugar derivatives.

10. The method of claim 1, comprising applying DHEA to the human superficial body growths.

11. The method of claim 1, comprising applying 5-androstene-3β,17β-diol to the human superficial body growths.

12. The method of claim 1, comprising applying 5-androstene-3β,17β-diol sulfate to the human superficial body growths.

13. The method of claim 1, comprising applying 4-androstene-3,17-dione to the human superficial body growths.

14. The method of claim 1, comprising applying pregnenolone to the human superficial body growths.

15. The method of claim 1, comprising applying 17α-hydroxypregnenolone to the human superficial body growths.

16. The method of claim 1, comprising applying DHEA sulfate to the human superficial body growths.

17. The method of claim 1, comprising applying 17α-hydroxypregnenolone sulfate to the human superficial body growths.

18. The method of claim 10, wherein the composition comprises from 0.1% to 5% by weight, relative to the total weight of the composition, of the DHEA.

19. The method of claim 11, wherein the composition comprises from 0.1% to 5% by weight, relative to the total weight of the composition, of the 5-androstene-3β,17β-diol.

20. The method of claim 12, wherein the composition comprises from 0.1% to 5% by weight, relative to the total weight of the composition, of the 5-androstene-3β,17β-diol sulfate.

21. The method of claim 13, wherein the composition comprises from 0.1% to 5% by weight, relative to the total weight of the composition, of the 4-androstene-3,17-dione.

22. The method of claim 14, wherein the composition comprises from 0.1% to 5% by weight, relative to the total weight of the composition, of the pregnenolone.

23. The method of claim 15, wherein the composition comprises from 0.1% to 5% by weight, relative to the total weight of the composition, of the 17α-hydroxypregnenolone.

24. The method of claim 16, wherein the the DHEA sulfate is applied in the form of a composition, and the composition comprises from 0.1% to 5% by weight, relative to the total weight of the composition, of the DHEA sulfate.

25. The method of claim 17, wherein the composition comprises from 0.1% to 5% by weight, relative to the total weight of the composition, of the 17α-hydroxypregnenolone sulfate.

* * * * *